United States Patent [19]

Kosaka

[11] Patent Number: 5,633,503
[45] Date of Patent: May 27, 1997

[54] PARTICLE ANALYZER

[75] Inventor: Tokihiro Kosaka, Kakogawa, Japan

[73] Assignee: TOA Medical Electronics Co., Ltd., Hyogo-ken, Japan

[21] Appl. No.: 346,268

[22] Filed: Nov. 23, 1994

[30] Foreign Application Priority Data

Nov. 26, 1993 [JP] Japan .................. 5-296936

[51] Int. Cl.$^6$ .................................. G01N 21/64
[52] U.S. Cl. .................. 250/458.1; 250/459.1; 250/461.2
[58] Field of Search ............... 250/458.1, 459.1, 250/461.2, 455.11

[56] References Cited

U.S. PATENT DOCUMENTS

| | | | |
|---|---|---|---|
| 4,999,513 | 3/1991 | Ito et al. | 250/575 |
| 5,247,339 | 9/1993 | Ogino | 250/461.2 |
| 5,260,029 | 11/1993 | Hosoi et al. | 250/461.2 |
| 5,260,764 | 11/1993 | Fukuda et al. | 250/461.2 |
| 5,270,548 | 12/1993 | Steinkamp | 250/461.2 |
| 5,436,717 | 7/1995 | Ogino | 356/72 |
| 5,471,294 | 11/1995 | Ogino | 356/73 |

FOREIGN PATENT DOCUMENTS

| | | |
|---|---|---|
| 5-79970 | 3/1993 | Japan . |
| 5-142137 | 6/1993 | Japan . |

*Primary Examiner*—Michael J. Tokar
*Assistant Examiner*—Virgil O. Tyler

[57] ABSTRACT

A particle analyzer includes a flow cell for enclosing a sample liquid containing particles in a sheathed flow to form a flat flow of the sample liquid; an exciting light source for emitting light for exciting fluorescence to irradiate the particle in the flat flow; a capturing device for capturing a fluorescent image of the particle when the particle reaches a predetermined position of the flat flow, the exciting light source and the capturing device being disposed so that a capturing optical axis of the capturing device is perpendicular to a surface of the flat flow and orthogonal to a light emitting optical axis of the exciting light source; and a shutter device for allowing the capturing device to receive the fluorescence from the particle for a predetermined period of time.

19 Claims, 7 Drawing Sheets

FIG. 10

PARTICLE ANALYZER

BACKGROUND OF THE INVENTION

1. Field of the Invention

The present invention relates to a particle analyzer, and more particularly to a particle analyzer for analyzing particles by allowing a sample liquid such as blood and urine containing particle components to flow through a flow cell and by irradiating the sample liquid with light to capture an image of the particles.

2. Description of the Related Art

Such particle analyzers are conventionally known in which a light source irradiates a sample liquid flow containing particles and a video camera captures a light-transmitting image of the particle irradiated with the light source (for example, see Japanese Published Unexamined Patent Application No. HEI 5-79970 and Japanese Published Unexamined Patent Application No. HEI 5-142137). However, the use of such conventional particle analyzers to capture fluorescence-emitting particles involves a problem in that direct light radiated from the light source to the video camera cannot be completely shielded, thereby making it difficult to obtain a fluorescent image which has a favorable S/N ratio.

SUMMARY OF THE INVENTION

The present invention has been conceived of in view of the aforementioned problem, and an object of the invention is to provide a particle analyzer that irradiates the particles with light for exciting fluorescence and captures the particles from the direction orthogonal to an optical axis of the light.

Therefore, the present invention provides a particle analyzer comprising: a flow cell for enclosing a sample liquid containing particles in a sheathed flow to form a flat flow of the sample liquid; exciting light source means for emitting light for exciting fluorescence to irradiate the particle in the flat flow; capturing means for capturing a fluorescent image of the particle when the particle reaches a predetermined position of the flat flow, the exciting light source means and the capturing means being disposed so that a capturing optical axis of the capturing means is perpendicular to a surface of the flat flow and orthogonal to a light emitting optical axis of the exciting light source; and shutter means for allowing the capturing means to receive the fluorescence from the particle for a predetermined period of time.

DESCRIPTION OF THE BRIEF DRAWINGS

The present invention will be detailed in conjunction with the accompanying drawings.

DESCRIPTION OF THE PREFERRED EMBODIMENTS

Particles to be analyzed by the particle analyzer of the present invention refer to mineral particles and organic particles such as blood cells or cells. Preferably, the particles are preliminarily stained with a fluorescent dye or labeled by a fluorescence emitting substance. But the particles are not always stained with the dye when the particles are cells which inherently contain a fluorescence emitting dyestuff such as lipofuscin or porphyrin.

The flow cell enclosing a sample liquid flow containing particles in a sheathed flow converts the sample liquid flow into a flat flow with a hydrodynamic effect.

Preferably, the flow cell of the present invention can configure the sample liquid flow into a flat flow having a thickness approximately equal to the particle diameter and a width equal to about ten times the particle diameter, and allow the sample liquid flow to flow at a rate of 50 to 200 mm/sec. The capturing device can capture fluorescent images of the particles at all times just in focus, since the optical path between the capturing device and the particle in the flat flow is not so varied.

The exciting light source device may be a laser beam light source for consecutively emitting light (not the pulse light emission).

A video camera for capturing a general two dimensional image may be used as the capturing device. In such a case, preferably, the video camera may provide an image intensifier (image intensifying means) for intensifying a feeble fluorescent image thereof. In addition, preferably, the image intensifier may include a shutter.

Preferably, as the shutter, an electronic shutter may be used which has a shutter speed variable within the scope of 1 to 10 μsec.

The shutter may be constituted to operate (open and close) in a certain cycle (for example, every 1/30 sec). Preferably, the shutter may operate based on a detecting signal from means for optically detecting that the particles traveling with the sample liquid flow reach a predetermined position where the capturing device can capture an image of such particles.

The particle analyzer of the present invention may comprise, either separately or integrally, the capturing means and the image intensifying means.

In addition, the particle analyzer of the present invention may further comprise light detection means for detecting light which comes from the particle irradiated with the exciting light; a controller for controlling an operational timing of the shutter based on a detection signal from the light detection and an analyzer means for analyzing the particle based on at least one of an image signal from the capturing device and the detection signal from the light detector.

The light which comes from the particle may be forward scatter light, side scatter light, forward fluorescence or side fluorescence.

The particle analyzer may further include an illumination light source for emitting illumination light to irradiate the particle in the flat flow, a light illumination optical axis of the illumination light source being perpendicular to a surface of the flat flow; a one dimensional image sensor for receiving the illumination light passing through the particle to capture an image of the particle by scanning across the flat flow a plurality times a controller for controlling an operation timing of the shutter based on an image signal from the one dimensional image sensor; and analyzing means for analyzing the particle based on at least one of image signals from the capturing device and the one dimensional image sensor.

The capturing device may capture the fluorecent image obtained from one surface of the flat flow and the light detector may detect the light obtained from the other surface of the flat flow.

The particle analyzer of the present invention may also include; a flow cell for enclosing a sample liquid containing particles in a sheathed flow to form a flat flow of the sample liquid; exciting light source for consecutively irradiating the particle in the flat flow with light for exciting fluorescence; a capturing device for capturing a fluorescent image of the particle when the particle reaches a predetermined position of the flat flow, the exciting light source and the capturing device being disposed so that a capturing optical axis of the capturing device is perpendicular to a surface of the flat flow and orthogonal to a light emitting optical axis of the exciting light source; a shutter for allowing the capturing device to receive the fluorescence from the particle for a predetermined period of time; a light detector for detecting fluorescence and/or side scatter light coming from the particle irradiated with the exciting light; an illumination light source for irradiating the particle in the flat flow with illumination light, a light illumination optical axis of the illumination light source means being perpendicular to a surface of the flat flow; a one dimensional image sensor for receiving the illumination light through the particle to capture an image of the particle by scaning across the flat flow a plurality of times; a controller for controlling an operation timing of the shutter based on at least one of a detector signal of the light detection and an image signal of the one dimensional image sensor; and an analyzer for analyzing the particle based on at least one of the image signals from the capturing device and one dimensional image sensor and the detection signal from the light detector.

Since the exciting light source for emitting light for exciting fluorescence irradiates the particle from a narrow width side of the flat flow of the flow cell, a light beam of the exciting light source can be focused thinly to a limited irradiation area with the result that the irradiation intensity of exciting light can be heightened at the irradiation area. Consequently, the exciting light source can efficiently irradiate the irradiation area without any loss. This increases the intensity of fluorescence emission from the particles so that a fluorescent image of the particle can be captured with a favorable S/N ratio.

Furthermore, the capturing device captures the fluorescent image of the particle from a wide side of the flat flow, that is, the optical axes of the capturing device and the exciting light source are orthogonal to each other. Consequently, since the light from the exciting light source means does not directly strike the capturing device, the capturing device can capture a fluorescent image of the particle with a favorable S/N ratio almost free from an influence of the exciting light.

The present invention will be detailed by using embodiments 1 through 5 shown in the accompanying drawings. However, they are not intended to limit the scope of the present invention. In the drawings showing embodiments 1 through 5, like numerals designate like constituents to avoid repeated description thereof.

EMBODIMENT 1

Figure 1:
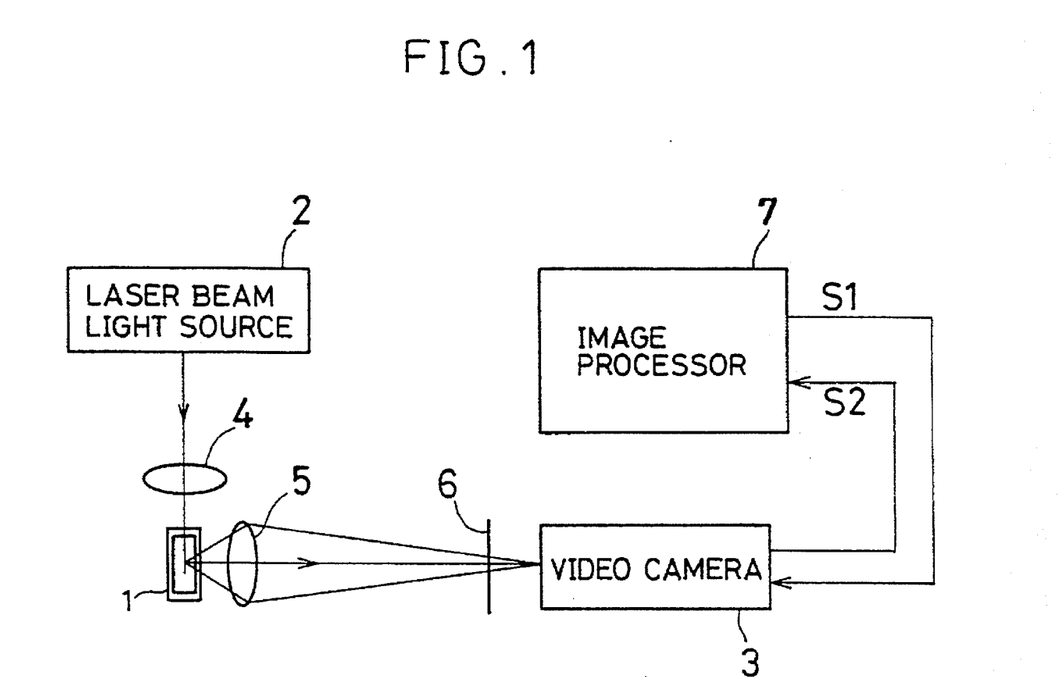
FIG. 1 is a view illustrating a structure of a particle analyzer according to a first embodiment of the present invention.

FIG. 1 is a view illustrating a particle analyzer in accordance with a first embodiment of the present invention. A flow cell 1 encloses a sample liquid flow containing particles dyed with a fluorescence dye in a sheathed flow to convert the sample liquid flow into a flat flow having a thickness of about 10 μm and a width of about 150 μm (in FIG. 1, the sample liquid flow flows from a surface side of the paper to a rear side thereof). A laser beam light source 2 consecutively emits light for exciting fluorescence to irradiate the particles from a narrow side of the flat flow. This is, for example, an Ar laser emitting a beam having a wavelength of about 488 nm, and a beam diameter of about 1.0 mm. A video camera 3 captures a fluorescent image of the particle by receiving fluorescence from a wide side of the flat flow when the particles traveling in the sample liquid flow reaches a predetermined position where the image thereof can be captured.

The video camera 3 (an intensified video camera) incorporates an intensifier for intensifying the intensity of the received light tens of thousands of times and an electronic shutter (having a shutter speed variable within the scope of 1 to 10 μsec) for capturing an image free from blurs. FIG. 1 further shows a condenser lens 4 for focusing a beam (1.0 mmØ) emitted from the laser beam light source 2 into a beam having a diameter of about 20 μm to irradiate the sample liquid flow, an objective lens 5 for forming on a capturing surface of the video camera 3 a fluorescent image of the particles present in a predetermined capturing area, and an interference filter 6.

An image processor 7 processes a video signal S2 transmitted from the intensified video camera 3 and outputs a gate control signal (electronic shutter driving signal) S1 to the intensified video camera 3 to open a gate (electronic shutter) at the frame rate (for each 1/30 seconds) of the video camera 3.

In this particular embodiment, the objective lens 5 is arranged for capturing a fluorescent image of particles in a direction perpendicular to the direction of an optical axis of the laser beam as shown in FIG. 1. In other words, the fluorescent image is captured from the wide side of the flat flow of the flow cell 1. Thus, the direct light of the laser beam (exciting light) is not incident on the objective lens 5. This prevents the S/N ratio of the fluorescent image of particles from being reduced under the influence of the exciting light.

When the light emitted from the laser beam light source 2 is incident on the flow cell 1 through the condenser lens 4 so that the particles are irradiated with the laser beam, the fluorescence is excited from the particles. The excited fluorescence passes through the objective lens 5 to form the fluorescent image on the capturing surface of the intensified video camera 3. The interference filter 6 arranged between the objective lens 5 and the video camera 3 shields the exciting light which leaks to the side of the filter 6, while selecting and receiving the fluorescence within a certain range of wavelength.

The intensified video camera 3 obtains the fluorescent image of the particles free from blurs by opening the gate (shutter) only for a moment when the particles are present in an area irradiated with the exciting light. Such period for which the gate is open should be shortened as the traveling speed of the particles becomes high. In correspondence to the shortened period for which the gate is open, the fluorescence accumulation time on the capturing surface becomes shorter, and thereby a S/N ratio of the fluorescent image of the particles is reduced. The flow rate of the sample liquid flow in this embodiment is slowed down by a considerable degree compared with conventional flow cytometers, thereby saving the fluorescenece accumulation time. Although the S/N ratio of the fluorescent image is improved with the slower flow rate of the sample liquid flow, but the amount of sample analysis per unit time decreases. Therefore, the present invention is intended to offset a decrease in the amount of analysis by configuring the sample liquid flow into a flat flow in the flow cell.

The image intensifier of the video camera 3 intensifies several thousand to tens of thousands of times the intensity of the feeble fluorescent image formed on the capturing surface of the intensified video camera 3. The image processor 7 processes the captured fluorescent image to analyze the intensity of the fluorescence and the fluorescence emitting portion. Since the structure shown in FIG. 1 does not provide a function of monitoring whether the particles are passing through the capturing area (irradiated with the laser beam), the intensified video camera 3 opens the gate with the gate control signal S1 output from the image processor 7 in a constant cycle of 1/30 seconds. When the particles are present in the area irradiated with the laser beam just at the time of gate opening, the fluorescent image of particle is captured.

Embodiments 2 through 5 described hereinbelow further provides a monitoring system for monitoring whether the particles are passing through the area (corresponding to the capturing area of the intensified video camera) which is irradiated with the laser beam.

The monitoring system provides a function of avoiding the capturing of trash and small dust so that the gate of the intensified video camera 3 is open when particles to be captured enter the area irradiated with the laser beam. Thus, it becomes possible to capture with good efficiency only particles to be measured without overlooking them by providing such monitoring system.

EMBODIMENT 2

Figure 2:
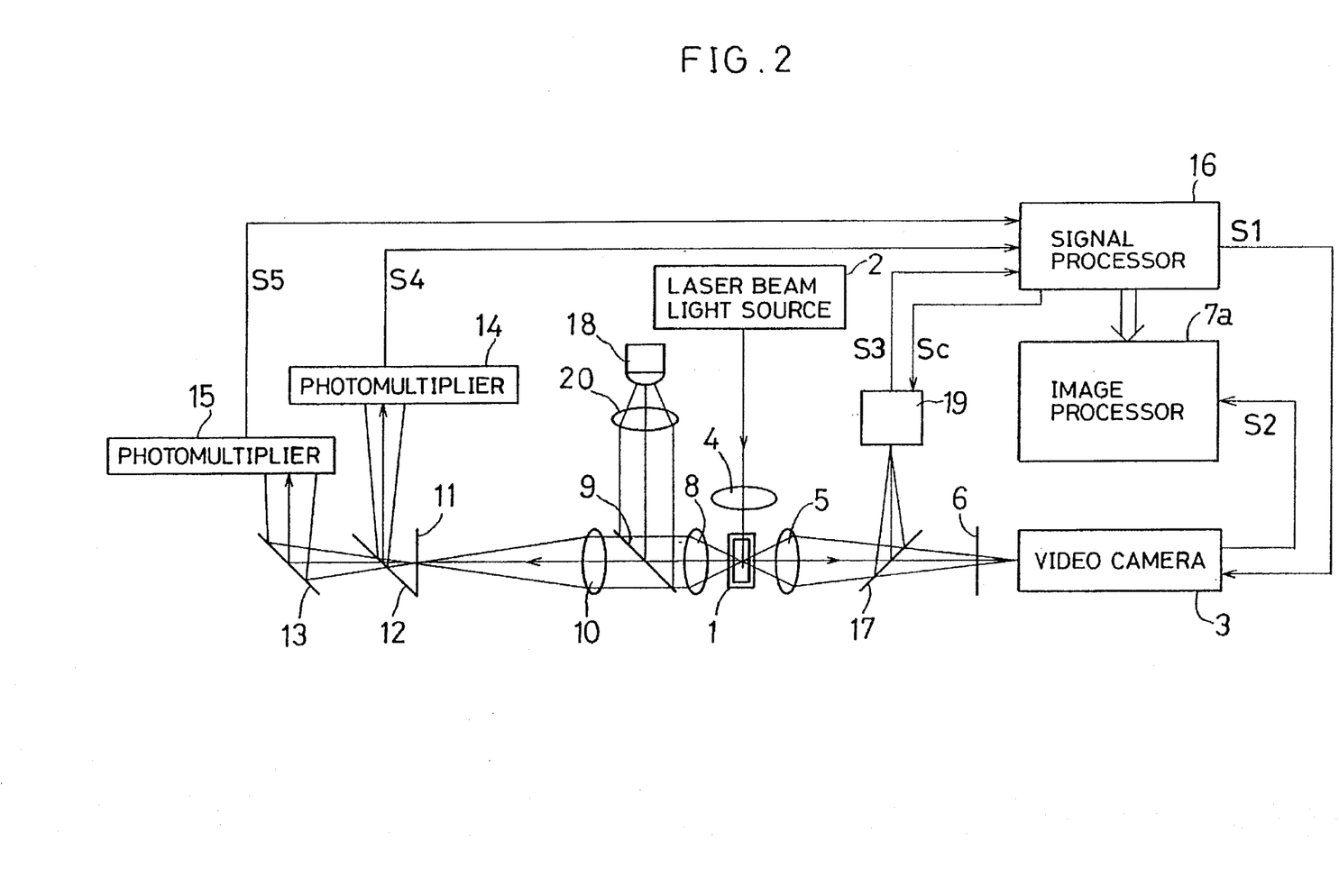
FIG. 2 is a view illustrating a structure of the particle analyzer according to a second embodiment of the present invention.

FIG. 2 is a view illustrating a structure of a particle analyzer according to a second embodiment of the present invention. The particle analyzer according to the second embodiment is a system in which a particle passage monitoring system, a fluorescence intensity detecting system, and a side scatter light intensity detecting system are added to the first embodiment.

As shown in FIG. 2, the condenser lens 4 focuses light emitted from the laser beam light source 2 for exciting particles dyed with the fluorescent dyes in the same manner as the particle analyzer according to embodiment 1 (shown in FIG. 1). When the particles dyed with the fluorescent dye pass through an area which is irradiated with the laser beam, fluorescence is excited and side scatter fluorescence of the particles is collected with the objective lenses 5 and an objective lens 8 arranged in the direction perpendicular relative to the optical axis of the laser beam from the laser beam light source 2.

The fluorescence caught by the objective lens 8 passes through a dichroic mirror 9 and an image forming lens 10 to form an image on a slit 11. The slit 11 limits an area for detecting the fluorescence. A dichroic mirror 12 reflects the fluorescence having a wavelength of red color to be received and converted into a red fluorescence detecting signal S4 by a photomultiplier 14. The dichroic mirror 12 transmits the fluorescence having a wavelength of green color or the side scatter light, which is reflected by a dichroic mirror 13 and converted into a green fluorescence or side scatter light detecting signal S5 by a photomultiplier 15.

The red fluorescence detecting signal S4 and the green fluorescence or side scatter light detecting signal S5 are transmitted to a signal processor 16 and A/D converted into the same information as obtained by a conventional flow cytometer.

On the other hand, the fluorescence caught by the objective lens 5 passes through a dichroic mirror 17 and reaches the filter 6. The fluorescence, having a wavelength selected by the filter 6, forms a fluorescence image on the capturing surface of the video camera 3. As mentioned above, the flow cell 1 encloses the sample flow in the sheathed flow to convert the sample flow into the flat flow. This increases the possibility that two or more particles pass through the area irradiated with the laser beam. Therefore, the obtained information of the fluorescence intensity does not accurately represent an individual fluorescence intensity of each particle, since the information integrally includes the fluorescence intensities of two or more particles.

Figure 6:
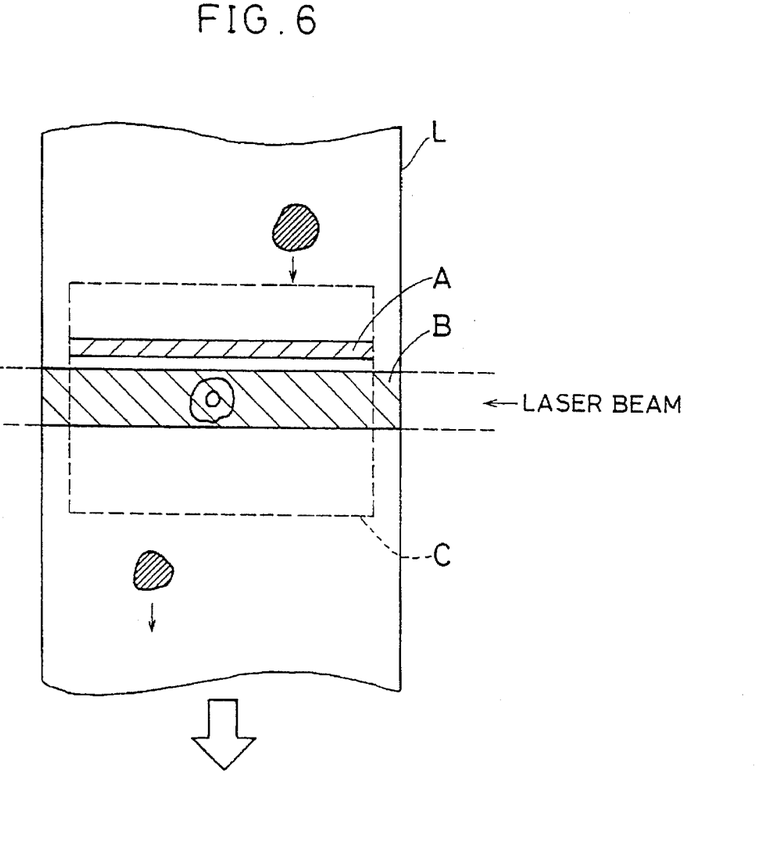
FIG. 6 is a view illustrating a structure of a detection area irradiated with a sample liquid flow laser light.

FIG. 6 shows operations of the particle passage monitoring system to monitor whether two or more particles pass through an area B of the sample flow L at the same time when the area B is irradiated with the laser beam. This monitoring system includes a light source 18, a collimator lens 20, and a line sensor (one dimensional camera) 19 as shown in FIG. 2.

The light source 18 emits light, for example near-infrared light, which has a wavelength in the range which does not involve the wavelength of the laser beam or the fluorescence. The light emitted from the light source 18 is collimated by the collimator lens 20, reflected by the dichroic mirror 9 and focused on the sample flow by the objective lens 8. As shown in FIG. 6, an area A irradiated with the light source 18 is set at the slightly upper side of the area B irradiated with the laser beam and a detection area of the line sensor 19 is set to correspond to the area A. The light passing through the area A is forcused on a light receiving surface of the line sensor 19 through the dichroic mirror 17. The dichroic mirrors 9 and 17 have characteristics reflecting light having the wavelength of the light emitted from the light source 18. An area C shown in FIG. 6 is an area captured with the video camera 3.

Figures 9A, 9B, 9C:
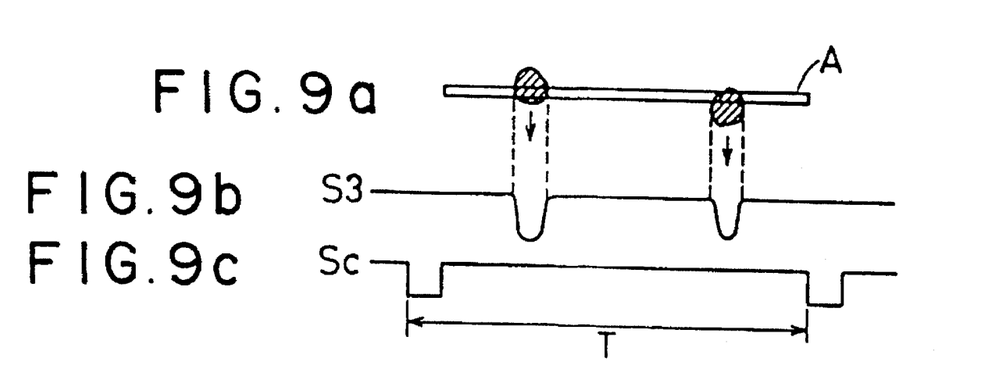
FIG. 9a illustrates two particles simultaneously passing through an area in the second embodiment.
FIG. 9b is a waveform of a detection signal detected by a line sensor in the second embodiment.
FIG. 9c is a waveform of a scanning signal for a line sensor in the second embodiment.

FIG. 9a shows a state in which two particles are passing through the area A at the same time. FIG. 9b shows an example of a detecting signal S3 output from the line sensor 19. FIG. 9c shows an example of a scanning signal Sc input to the line sensor 19. Every time the line sensor 19 receives the scanning signal Sc (of which cycle T is several tens µ sec) from a signal processor 16, the detecting signal S3 is output from the line sensor 19 to the signal processor 16. The signal processor 16 converts the detecting signal S3 into a binary code signal to judge whether two or more particles are passing through the area A at the same time. Judging that two or more particles are passing through the area A at the same time, the signal processor 16 ignores the fluorescence intensity information or the side scatter light intensity information obtained from the signals S4 and S5 of the photomultipliers 14 and 15.

The above particle passage monitoring system not only monitors the simultaneous passage of the particles, but calculates information such as an area, roundness and light absorbency of each particle by processing the detecting signal S3.

Figure 10:
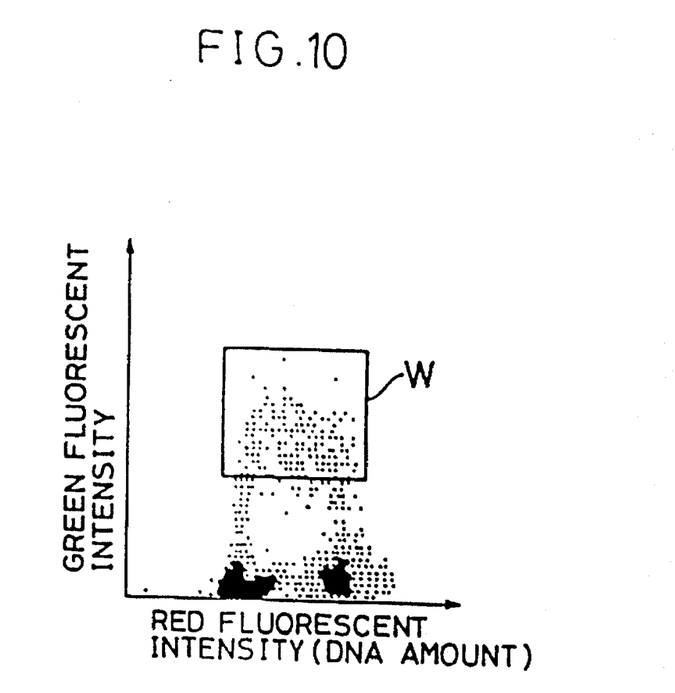
FIG. 10 is a scattergram of fluorescence intensity in the second embodiment.

This system can also distinguish a specified group of particles in real time by combining these information and fluorescence intensity information obtained from the A/D converted signals S4 and S5. For example, this system can easily distinguish the cells which are in the breeding season from the particles in the sample flow to analyze morphology of the nuclei based on the fluorescence images of the cells. FIG. 10 shows an example of scatter diagram of which horizontal and vertical axes are graduated with a red fluorescence intensity representing a guantity of DNA and a green fluorescence intensity representing a quantity of breeding antigen such as Br, dU of Ki-57, respectively. The fluorescent images of the cells in the breeding season can restrictively be obtained, when this system has a function for specifying a group of breeding cells in real time by using a window W as shown in FIG. 10.

Figure 7A:
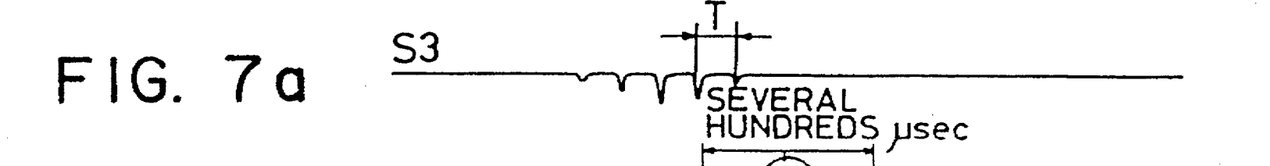
FIGS. 7a–7d are timing charts of each type of signal in the second embodiment.
Figure 7B:
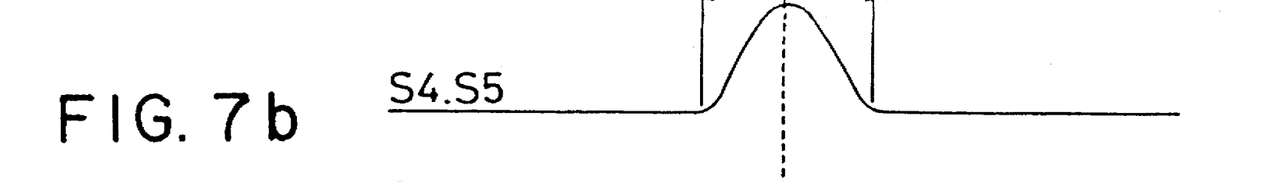
Figures 7C, 7D:
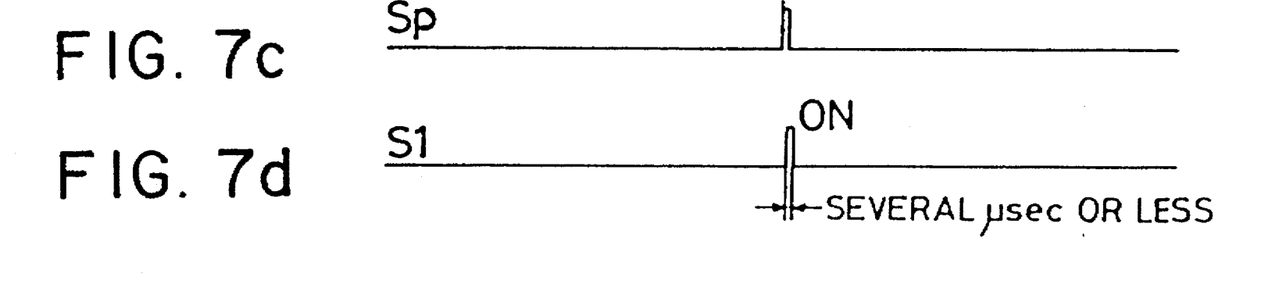

FIG. 7a shows the detecting signal S3 obtained when one of the particles is passing through the area A. The detecting signal S3 includes a plurality of pulses having a cycle of several tens of μsec corresponding to the scanning signal Sc (not shown in FIG. 7). This means that the line sensor 19 scans one particle a plurality of times. FIG. 7b shows the fluorescence detecting signals S4, S5 having a probe width of several hundred μsec. FIG. 7c shows the peak detecting signal Sp of the fluorescence detecting signal S4, S5. FIG. 7d shows the gate control signal for opening the shutter for several μsec or less.

Figure 8:
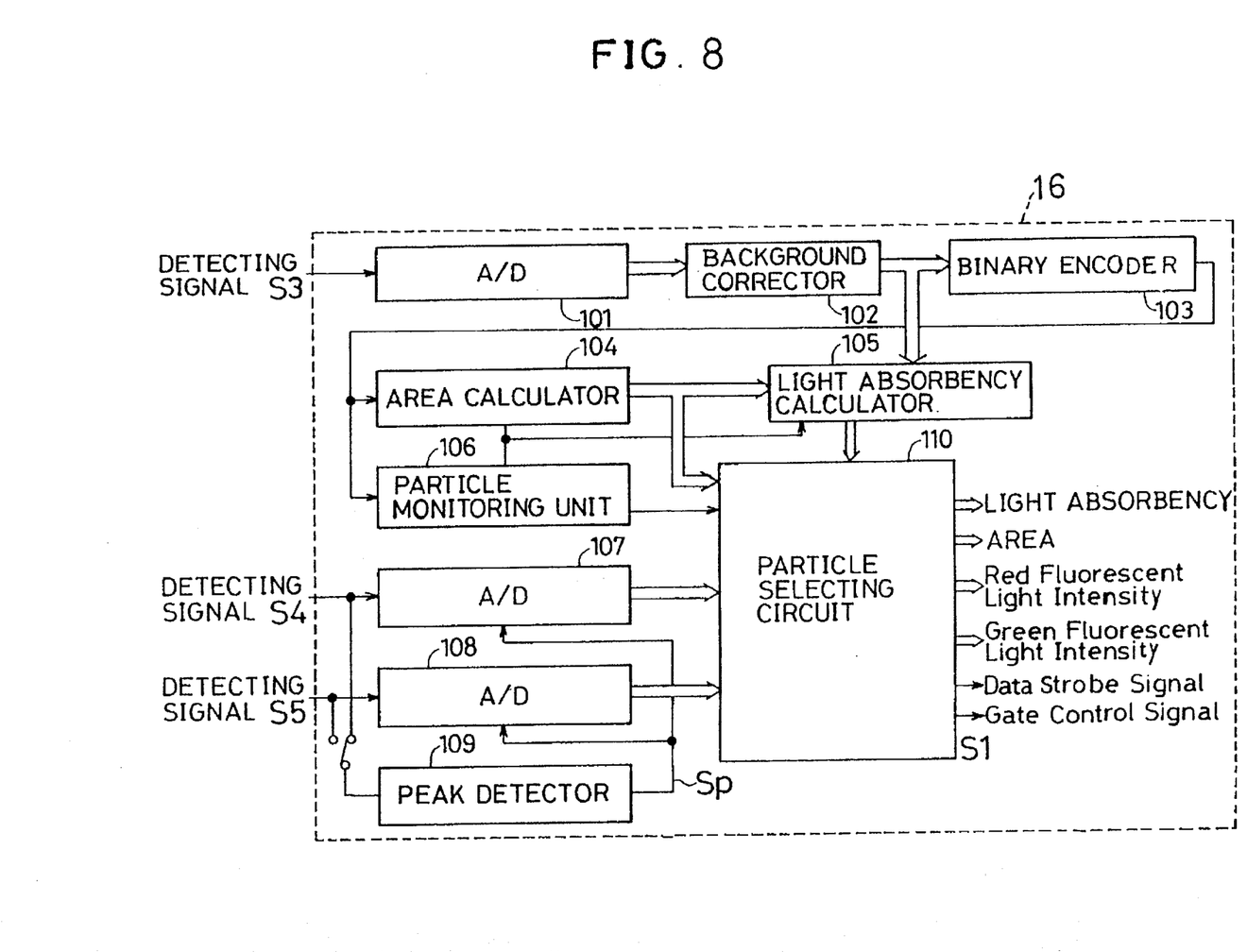
FIG. 8 is a block diagram showing a signal processor in the second embodiment.

FIG. 8 shows a block diagram of the signal processor 16 which processes the detecting signals S3, S4 and S5 to calculate information of an area or light absorbency of the particle.

An A/D converter 101 samples the detecting signal S3 based on a pixel clock signal to convert it into a digital signal. The digital signal is corrected through a background corrector 102 and binary encoded through a binary encoder 103. The background corrector 102 corrects the shading of the irradiation of the area A and the irregularity of the sensibility of each pixel of the line sensor 19. Concretely, the background corrector 102 previously stores the detecting signal S3 obtained at one scanning when no particle passes through the area A and performs the background correction by subtracting the detecting signal S3 obtained when the particle passes through the area A from the stored signal. The detecting signal S3, after corrected by the background corrector 102, is compared with a threshold level and binary encoded.

A particle monitoring unit 106 specifies the signal corresponding to each particle and judges whether two or more particles has passed through the area A, based on the binary encoded signal.

An area calculator 104 calculates a projected area of the particle by summing up pulse widths of the binary encoded signals with respect to one particle.

A light absorbency calculator 105 sums up correction data of one particle obtained by the background corrector 102 to calculate a light absorbency of the particle by dividing the sum by the area of the particle.

A peak detector 109 detects each peak of the fluorescent detecting signals S4 and S5 to output each peak detecting signal Sp (shown in FIG. 7c), which is immediately A/D converted by A/D converters 107 or 108.

Since all the data, that is, the area, absorbency and the like have been obtained by this time, a particle selecting circuit 110 instantly (for several hundred nsec) judges whether the detected particle is a specified particle to be examined by combining these data and the fluorescent intensity data. The circuit 110 does not perform the judgement of the particle when the line sensor 19 detects that two or more particles are passing through the area A at the same time because the fluorescent intensity data lack reliability.

The circuit 110, when judging that the detected particle is a particle to be examined, outputs the gate control signal S1 (shown in FIG. 7d) to permit the video camera 3 to open the shutter during several μsec.

It takes a processing time of several μsec or less until the video camera 3 opens the shutter after the peak signal Sp was detected. Therefore, the particle exists near the center of the area A while the shutter opens. Then, the intensified video camera 3 receives fluorescence emitted from the particle to intensify the fluorescence and capture a fluorescent image of the particle.

The video signal S2 is transmitted from the video camera 3 to an image processor 7a which performs various processes for picking up each particle image off the captured image to store the particle image, obtaining morphological information of the particle and the like.

The processor 7a receives the information obtained by the signal processor 16, that is, the data with respect to the area, fluorescence intensity, light absorbency and the like to display a two dimensional histogram and scatter diagram as shown in FIG. 10. The processor 7a may further include functions for setting a window in the displayed scatter diagram to capture fluorescent images of a specified group of particles and displaying the captured fluorescent images of the particles. The analysis means of the present invention includes the image processor 7a and the signal processor 16.

EMBODIMENT 3

Figure 3:
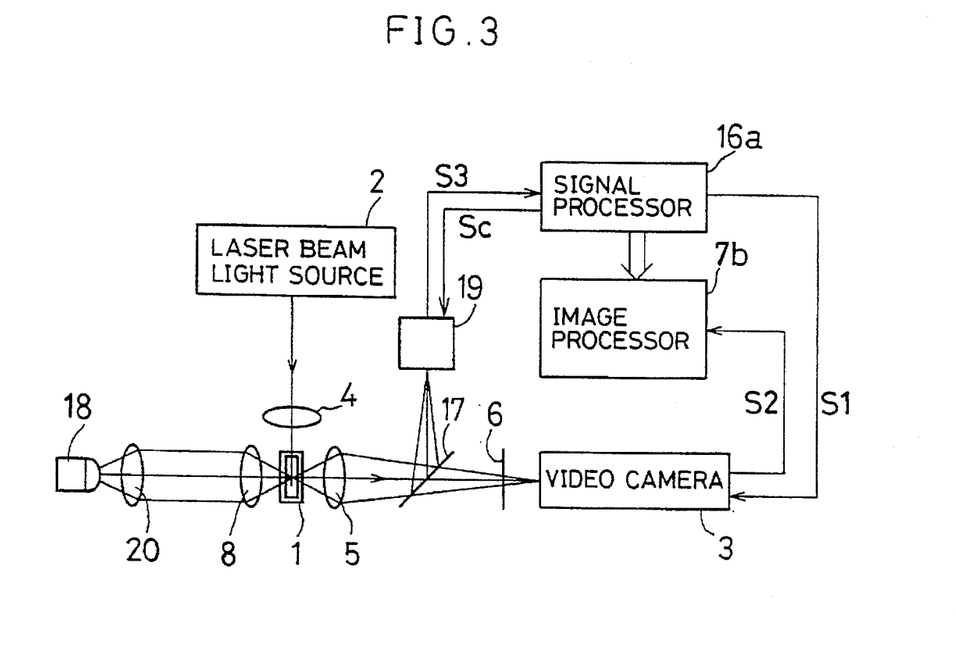
FIG. 3 is a view illustrating a structure of the particle analyzer according to a third embodiment of the present invention.

FIG. 3 is a view showing a structure of the particle analyzer according to a third embodiment of the present invention, which is structured by removing the fluorescence detection system from the second embodiment. As shown in FIG. 6, the collimator lens 20 collimates light emitted from the light source 18. The condenser lens 8 focuses the collimated light to irradiate the area A from the wide side of the sample flow L. In the sample liquid flow L the area A irradiated with light coming from the light source 18 is set a little upstream of the area B irradiated with the fluorescence exciting laser beam in the same manner as in the second embodiment.

The dichroic mirror 17 reflects light passing through the area A via the objective lens 5 thereby forming an image on the photodetecting surface of the line sensor 19. When the particle passes through the area A, the detecting signal S3 as shown in FIG. 7 is obtained since the light accumulation with respect to the photodetecting surface of the line sensor 19 is varied. While one particle passes through the area A, the line sensor 19 scans the particle several times.

A signal processor 16a processes the detecting signal S3 output from the line sensor 19 to detect information on the particle such as a size (area), roundness, light absorbency and the like when the particle passes through the area A. Judging that the particle is a particle to be captured based on the aforementioned information, the signal processor 16a timely outputs the gate control signal S1 while the particle travels in the area B irradiated with the laser beam so as to permit the intensified video camera 3 to open the gate (shutter). When the sample flow flows at a rate of 100 mm/sec, a fluorescent image of the particle can be captured which is almost free from blurs (for example, with respect to particles having a diameter of 10μ, the capturing blur is suppressed to 5% of the particle diameter.

EMBODIMENT 4

Figure 4:
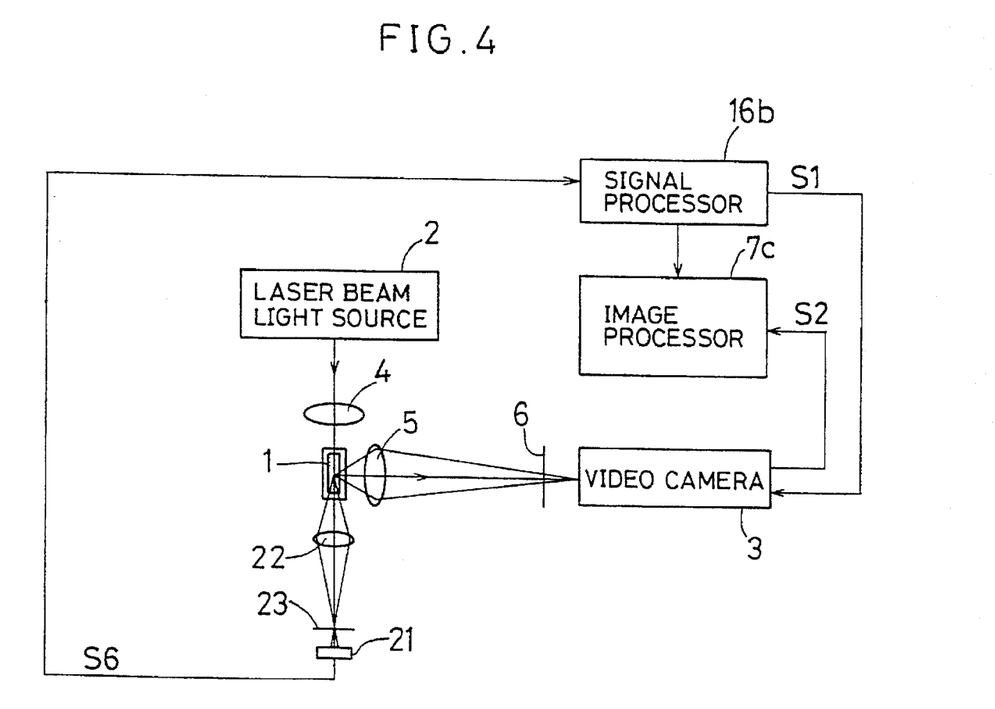
FIG. 4 is a view illustrating a structure of the particle analyzer according to a fourth embodiment of the present invention.

FIG. 4 is a view showing a structure of a particle analyzer according to a fourth embodiment which is structured by adding to the first embodiment, a photodiode 21 for detecting a forward scatter light intensity from the particles which pass through the area B to be irradiated with the laser beam and a signal processor 16b for processing a detecting signal S6 output from the photodiode 21. The photodiode 21 receives the forward scatter light from the particles through an objective lens 22 and a pinhole 23. The pinhole 23 is provided to receive only scatter light scattered by the particle and reject reflection light or refraction light of the flow cell 1. The analyzer can be designed to detect forward fluorescence in place of the forward scatter light.

The signal processor 16b receives the forward scatter light detecting signal S6 to determine the magnitude of the signal S6 in real time. When the peak of the forward scatter light intensity detecting signal S6 ranges in a certain scope, a judgment is passed that the particle is an object to be measured. Then the gate control signal S1 is output to the intensified video camera 3, which immediately opens the gate for capturing a fluorescent image of the particles. Time is very short from the moment when the intensity of scatter light from particles reaches a peak until the moment when the gate of the intensified video camera is opened. Consequently, the fluorescent image can be captured while the particle is present in the area B irradiated with the laser beam.

Furthermore, the signal processor 16b processes signals for particle analysis upon receipt of the forward scatter light detecting signal S6. An image processor 7c analyzes data and processes images for particle analysis upon receipt of the information on the scatter light intensity and the video signal S2 from video camera 3.

EMBODIMENT 5

Figure 5:
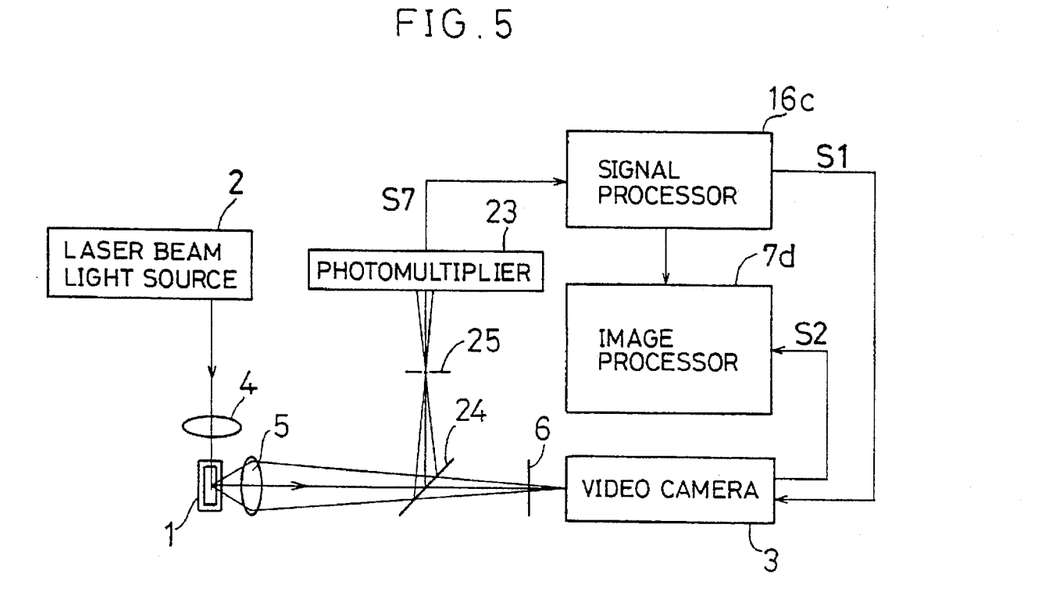
FIG. 5 is a view illustrating a structure of the particle analyzer according to a fifth embodiment of the present invention.

FIG. 5 is a view showing a structure of a particle analyzer according to a fifth embodiment of the present invention, which is structured by adding to the first embodiment a photomultiplier 23 for detecting an intensity of side scatter light when the particle passes through the area B to be irradiated with the laser beam (FIG. 6), a signal processor 16c for processing a detection signal S7. The objective lens 5 collects the side scatter light from the particles, and a dichroic mirror 24 reflects the light. Then the photomultiplier 23 receives the light through a slit 25. The slit is provided so that the photomultiplier 23 receives only the side scatter light scattered by the particle and fails to receive as little as possible light reflected and refracted by the flow cell 1. It is easy to detect side fluorescence in place of the side scatter light. Preferably, the light is detected from the side opposite to the side at which the fluorescent image is captured.

The side scattered light detecting signal S7 is transmitted to the signal processor 16c, which determines the magnitude of the signal S7 in real time. When the peak of the signal S7 ranges in a certain scope, a judgement is passed that the particle is a particle to be measured so that the intensified video camera 3 opens the gate for capturing the fluorescent image based on the gate control signal S1. Time is very short from the moment when the intensity of the scattered light reaches the peak until the gate of the intensified video camera 3 is opened with the result that the fluorescent image is captured while the particles are present in the area B to be irradiated with the laser beam (shown in FIG. 6).

Furthermore, the signal processor 16c, upon receipt of the side scattered light detecting signal S7, processes the signal which is required for the particle analysis. An image processor 7d analyzes data and processes images in order to analyze the particle upon receipt of the video signal S2 from the intensified video camera 3 and the information on the intensity of the side scatter light from the signal processor 16c.

The particle analyzer of the present invention has the following characteristics.

1. The particle analyzer can secure the amount of the sample to be analyzed per unit time without raising the flow rate of the sample liquid flow by configuring the sample flow containing the particles into a flat flow.

2. The particle analyzer focuses the exciting light (laser beam) to a limited area to irradiate the flat flow with the light from the narrow side of the flat flow and can raise the intensity of the exciting light illumination thereby capturing a fluorescent image with a favorable S/N ratio.

3. When the particles are cells, the particle analyzer can obtain information on the morphology of particle nuclei from the captured fluorescent image by staining the nuclei with a fluorescent dye.

4. The particle analyzer can detect that the particles are passing through the area where the fluorescent image of the particles are captured, by adding a scattered light detection system and a line sensor detection system and capture the fluorescent image with good efficiency by selecting only particles to be captured.

5. the particle analyzer can simultaneously obtain the particle size (area), roundness and light absorption by using a line sensor.

6. The particle analyzer can easily perform the following analysis by adding a function of fluorescence and side scatter light intensity detecting function in addition to the fluorescent image capturing function. The particle analyzer is useful as a support apparatus supporting biological research on the behavior of cancer cells or the like.

1) Relation between the morphology of the nuclei of cancer cells and the amount of DNA, 2) development site (localization) of breeding antigens in cells in the S period, 3) analysis of the development and behavior of cancer gene products (tumor marker), 4) analysis of the development and behavior of cell surface antigens, 5) relation between cancer cells and bonding molecules, 6) relation between virus infection and canceration, 7) safety test of medical products (small nucleus test), 8) chromosome examination using DNA probes dyed with a fluorescence label (FISH), and 9) measurement of fine planktons (types, number, size, morphology, chlorophil amount or the like).

The present invention thus being described in conjunction with embodiments, it is our intention that the invention be not limited to any of the details of the description, unless otherwise specified, but rather be constructed broadly within its spirits and scope of the accompanying claims.

What is claimed is:

1. A particle analyzer comprising:
    a flow cell for enclosing a sample liquid containing particles in a sheathed flow to form a flat flow of the sample liquid;
    exciting light source means for emitting light for exciting fluorescence to irradiate the particle in the flat flow;
    an illumination light source for emitting illumination light to irradiate the particle in the flat flow;
    a sensor for receiving the illumination light passing through the particle to capture an image of the particle;
    monitoring means for determining whether two or more particles are passing through the flat flow imaged onto said sensor; and
    capturing means for capturing a fluorescent image of the particle when the particle reaches a predetermined position of the flat flow.

2. A particle analyzer according to claim 1 further comprising:
    a shutter which allows the capturing means to receive the fluorescence from the particle for a predetermined period of time;
    light detection means for detecting light coming from the particle irradiated with the exciting light;
    control means for controlling an operational timing of the shutter based on at least one of a detection signal from the light detection means and an image signal of said sensor; and
    analyzing means for analyzing the particle based on at least one of an image signal from each of the capturing means and said sensor and the detection signal from the light detection means.

3. A particle analyzer according to claim 2 wherein the light coming from the particle is at least one of forward scatter light, side scatter light, forward fluorescence and side fluorescence.

4. A particle analyzer according to claim 1 further comprising:
    a shutter which allows the capturing means to receive the fluorescence from the particle for a predetermined period of time;
    control means for controlling an operation timing of the shutter based on an image signal from the sensor; and
    analyzing means for analyzing the particle based on at least one of image signals from the capturing means and the sensor.

5. A particle analyzer according to claim 2 wherein the capturing means captures a fluorescent image obtained from one surface of the flat flow and light detection means detects the light obtained from the other surface of the flat flow.

6. A particle analyzer according to claim 1, wherein said sensor is a one dimensional image sensor capturing an image of the particle by scanning across the flat flow.

7. A particle analyzer according to claim 6, wherein said analyzing means further comprises means for calculating physical characteristics of the particle, said analyzing means ignoring calculated physical characteristics when two or more particles are indicated by said monitoring means.

8. A particle analyzer according to claim 4, wherein said analyzing means comprises means for calculating physical characteristics of the particle.

9. A particle analyzer according to claim 1, wherein said monitoring means monitors an area upstream of said predetermined position.

10. A method of analyzing particles in a sample liquid comprising the steps of:
    enclosing the sample liquid in a sheathed flow to form a flat flow having a first side and a second side orthogonal to said first side;
    irradiating particles in the first side of the flat flow with exciting light;
    irradiating particles in the flat flow with illuminating light;
    imaging the illuminating light passing through the flat flow onto a sensor;
    determining whether two or more particles are passing through the flat flow imaged onto said sensor; and
    capturing an image of the second side of the flat flow including a fluorescent image of a particle irradiated by the exciting light when the particle reaches a predetermined position.

11. A method according to claim 10, further comprising:
    detecting light coming from the particle irradiated with the exciting light;
    controlling, in accordance with the detecting step, an operational timing of a shutter for allowing the capturing step to receive fluorescence from the particle for a predetermined period of time; and
    analyzing the particle based on at least one of an image signal from the capturing step and a detection signal from the detecting step.

12. A method according to claim 10, further comprising:
    analyzing the particles based on at least one of image signals from the capturing step and the imaging step.

13. A method according to claim 10, wherein said imaging step includes imaging the illuminating light onto a one dimensional image sensor.

14. A method according to claim 12, further comprising ignoring said analyzing step based on an image signal from the capturing step when the determining step determines two or more particles are present.

15. A method according to claim 12, further comprising calculating physical characteristics of a particle in the flat flow imaged onto said one dimensional image sensor.

16. A particle analyzer comprising:
    a flow cell for enclosing a sample liquid containing particles in a sheathed flow to form a flat flow of the sample liquid;
    an exciting light source for emitting light for exciting fluorescence to irradiate the particle in the flat flow;
    capturing means for capturing a fluorescent image of the particle when the particle reaches a predetermined position of the flat flow;
    a shutter which allows the capturing means to receive the fluorescence from the particle for a predetermined period of time;
    an illumination light source for emitting illumination light to irradiate the particle in the flat flow;
    a sensor receiving the illumination light passing through the particle to capture an image of the particle;
    control means for controlling an operation timing of the shutter based on an image signal from said sensor; and
    analyzing means for analyzing the particle based on at least one of image signals from the capturing means and said sensor, said analyzing means including means for calculating physical characteristics of the particle.

17. A method of analyzing particles in a sample liquid comprising the steps of:
    enclosing the sample liquid in a sheathed flow to form a flat flow;

irradiating particles in the flat flow with exciting light;

capturing a fluorescent image of a particle irradiated by the exciting light;

irradiating particles in the flat flow with illuminating light;

imaging the illuminating light passing through the flat flow onto a sensor; and analyzing the particles based on at least one of image signals from the capturing step and the imaging step, said analyzing step including, said analyzing step including calculating physical characteristics of a particle in the flat flow imaged onto said sensor.

18. A method according to claim 10, wherein said imaging step includes imaging an area upstream of said predetermined position.

19. A particle analyzer according to claim 16, wherein said physical characteristics include at least one of absorbency and area.

* * * * *